(12) United States Patent
Gokaraju et al.

(10) Patent No.: US 11,071,764 B2
(45) Date of Patent: Jul. 27, 2021

(54) **SYNERGISTIC DIETARY SUPPLEMENT COMPOSITIONS OF *SPHAERANTHUS INDICUS* AND *TERMINALIA CHEBULA* FOR LIVER HEALTH**

(71) Applicant: LAILA NUTRACEUTICALS, Vijayawada (IN)

(72) Inventors: Ganga Raju Gokaraju, Vijaywada (IN); Rama Raju Gokaraju, Vijayawada (IN); Venkata Kanaka Ranga Raju Gokaraju, Vijayawada (IN); Trimurtulu Golakoti, Vijayawada (IN); Kiran Bhupathiraju, Vijayawada (IN); Venkata Krishna Raju Alluri, Vijayawada (IN)

( * ) Notice: Subject to any disclaimer, the term of this patent is extended or adjusted under 35 U.S.C. 154(b) by 0 days.

(21) Appl. No.: 16/462,415

(22) PCT Filed: Nov. 20, 2017

(86) PCT No.: PCT/IN2017/050543
§ 371 (c)(1),
(2) Date: May 20, 2019

(87) PCT Pub. No.: WO2018/092159
PCT Pub. Date: May 24, 2018

(65) Prior Publication Data
US 2019/0365839 A1 Dec. 5, 2019

(30) Foreign Application Priority Data

Nov. 20, 2016 (IN) .............................. 201641035885

(51) Int. Cl.
| | |
|---|---|
| *A61K 36/28* | (2006.01) |
| *A61P 1/16* | (2006.01) |
| *A61K 9/00* | (2006.01) |
| *A61K 36/185* | (2006.01) |
| *A61K 36/19* | (2006.01) |
| *A61K 36/42* | (2006.01) |
| *A61K 36/48* | (2006.01) |
| *A61K 36/53* | (2006.01) |
| *A61K 36/61* | (2006.01) |
| *A61K 36/71* | (2006.01) |
| *A61K 36/75* | (2006.01) |
| *A61K 36/8962* | (2006.01) |

(52) U.S. Cl.
CPC ............ *A61K 36/28* (2013.01); *A61K 9/0056* (2013.01); *A61K 9/0095* (2013.01); *A61K 36/185* (2013.01); *A61K 36/19* (2013.01); *A61K 36/42* (2013.01); *A61K 36/48* (2013.01); *A61K 36/53* (2013.01); *A61K 36/61* (2013.01); *A61K 36/71* (2013.01); *A61K 36/75* (2013.01); *A61K 36/8962* (2013.01); *A61P 1/16* (2018.01)

(58) Field of Classification Search
None
See application file for complete search history.

(56) References Cited

U.S. PATENT DOCUMENTS

| | | | | |
|---|---|---|---|---|
| 2007/0122496 | A1* | 5/2007 | Managoli | A61K 36/185 424/725 |
| 2014/0147394 | A1* | 5/2014 | Chaudhary | A61K 36/24 424/43 |
| 2019/0038576 | A1* | 2/2019 | Baron | A61K 9/2846 |

FOREIGN PATENT DOCUMENTS

| | | | |
|---|---|---|---|
| IN | 52/CHE/2010 A | * | 5/2012 |
| WO | 2011/083397 A1 | | 7/2011 |
| WO | WO 2015/118557 | * | 8/2015 |

OTHER PUBLICATIONS

Samal, P. et al. Ethnopharmacological Studies of Tradtional Hepatoprotective Medicinal Plants . . . Int J of Pharmacy and Technology 3(2)1917-1987, Apr./Jun. 2011. (Year: 2011).*
Aggarwal B. et al. Identification of Novel Anti-Inflammatory Agents from Ayurvedic Medicine for Prevention of Chronic Diseases. Current Drug Targets 12(11)1-103, Oct. 2011. (Year: 2011).*
International Search Report dated Apr. 18, 2018 in connection with PCT/IN2017/050543, filed Nov. 20, 2017.

* cited by examiner

*Primary Examiner* — Ralph J Gitomer
(74) *Attorney, Agent, or Firm* — Kramer Amado PC (57) ABSTRACT

The invention discloses synergistic compositions comprising at least one component selected from extract(s) and fraction(s) or mixtures thereof derived from *Sphaeranthus indicus* in combination with at least one component selected from extract(s), fraction(s), active compound(s) or mixtures thereof derived from *Terminalia chebula* for improving the liver health. The invention further discloses method of improving the liver health in humans and animals by administering the compositions comprising at least one component selected from extract(s) and fraction(s) or mixtures thereof derived from *Sphaeranthus indicus* in combination with at least one component selected from extract(s), fraction(s), active compound(s) or mixtures thereof derived from *Terminalia chebula*.

14 Claims, 4 Drawing Sheets

FIG. 4C

SYNERGISTIC DIETARY SUPPLEMENT COMPOSITIONS OF *SPHAERANTHUS INDICUS* AND *TERMINALIA CHEBULA* FOR LIVER HEALTH

TECHNICAL FIELD OF THE INVENTION

The invention relates to synergistic compositions comprising at least one component selected from extract(s) and fraction(s) or mixtures thereof derived from *Sphaeranthus Indicus* in combination with at least one component selected from extract(s), fraction(s), active compound(s) or mixtures thereof derived from *Terminalia chebula* for improving the liver health. The invention further relates to method of improving the liver health in humans and animals by administering the compositions comprising at least one component selected from extract(s) and fraction(s) or mixtures thereof derived from *Sphaeranthus indicus* in combination with at least one component selected from extract(s) and fraction(s) or mixtures thereof derived from *Terminalia chebula*.

BACKGROUND OF THE INVENTION

Liver is the vital organ in human body and it performs a number of functions, which include metabolizing the endogenous and exogenous compounds for their easy elimination from the body. Liver also plays a major role in numerous other functions, which include detoxification, glycogen storage, plasma protein synthesis, hormone production. Its highly specialized tissue mostly consists of hepatocytes regulates variety of biochemical reactions including synthesis and breakdown of small and complex molecules. However, continuous exposure to xenobiotics sometimes leads to hepatic injury. Various factors that cause liver damage include viral hepatitis (most commonly hepatitis B), cirrhosis, and excessive consumption of alcohol or medicines such as acetaminophen. Acute hepatic injury caused by hepatotoxins is a further cause of progressive liver diseases. Hence, major emphasis is being given in the last few years for the development of newer treatments for liver diseases, and herbal dietary supplements and nutraceuticals for improving the liver health and functions.

*Sphaeranthus indicus* is an important plant species in the family of Asteraceae. It is also known as Gorakhmundi. It is a highly branched, strongly-scented annual herb with winged stem, obovate-oblong leaves and compound heads as flowers. The medicinally useful parts are root, bark, leaves, flowers, and seeds. The flowering and fruiting heads of *Sphaeranthus indicus* contains 7-α-Hydroxy-4, 11(13)-eudesmadien-12,6-olide or 7-hydroxyfrullanolide as a major compound. *S. indicus* is used in ayurvedic medicine for the treatment of hepatopathy, indigestion, bronchitis, epileptic convulsions etc.

*Terminalia chebula* is a medium to large deciduous tree native to South Asia. It is a widely used herb in Indian Traditional System of medicine called Ayurveda. It is a gentle purgative, astringent, stomachic, antibilious and alterative. It is used for treating flatulence, constipation, diarrhoea, digestive disorders, vomiting, enlarged liver and spleen, cough and bronchial asthma, and for metabolic harmony. The fruits of *T. chebula* are used in combination with *Emblica officinalis* and *T. bellerica* (under the name *Triphala*) as a digestive aid and relief from constipation. Chebulagic acid, Chebulinic acid, ellagic acid and gallic acid are the key phytochemicals in *Chebula* fruit.

Hepatoprotective and anti-oxidant potential of extracts of *Sphaeranthus indicus* was reported against carbon tetrachloride ($CCL_4$) induced liver damage, and paracetamol induced liver damage.

An herbal formulation containing *Cichorium intybus*, *Sphaeranthus indicus*, *Rosa gallica*, *Swertia chirata*, *Coriandrum sativum*, *Smilax chinensis*, *Rheum* and *emodi* was investigated for hepatoprotective activity on ($CCl_4$) induced liver damage (Int. J. Chem. Sci.: 7(2), 2009, 617-624).

The PCT patent publication WO2011074001A2 discloses an herbal hepatoprotective composition comprising *Andrographis paniculata; Curcuma longa; Glycyrrhiza glabra* and *Terminalia chebula*.

The sustainability and development of animal cultures (Aquaculture including Shrimp, fish etc.) Poultry, swine, cattle and others are largely at stake as significant ecological and pathological problems are increasing in majority of the producing countries. Prevention and control of diseases are now the priority for the durability of this industry. Issues such as Antibiotic residues, bacterial resistance and the international restrictions on the use of antibiotics are increasing. The most critical issue affecting the aqua cultivation is compromised/damaged liver in the affected animals. Use of natural herbal compositions to prevent diseases, protect liver from damage and improve liver health and to reduce or even eliminate the use of antibiotics will leads to better health and growth of aquatic animals.

There is a continuous need in the art to provide an alternative synergistic composition comprising highly effective herbal extracts which protects and detoxifies liver. Moreover, there is a need in the art for better treatment options that provide minimal side effects thereby making the option safe for human and animal consumption.

OBJECT OF THE INVENTION

Therefore the principal object of the present invention is to provide a Synergistic compositions comprising at least one component selected from extract(s) and fraction(s) or mixtures thereof derived from *Sphaeranthus indicus* in combination with at least one component selected from extract(s) and fraction(s) or mixtures thereof derived from *Terminalia chebula* for improving the liver health in humans and animals.

The further object of the invention is to provide methods of use of the Synergistic compositions comprising at least one component selected from extract(s) and fraction(s) or mixtures thereof derived from *Sphaeranthus indicus* in combination with at least one component selected from extract(s) and fraction(s) or mixtures thereof derived from *Terminalia chebula* for improving the liver health in humans and animals.

Yet another object of the invention is to provide a Synergistic compositions comprising extracts or fractions of *Sphaeranthus indicus* in combination with at least one extract or fraction derived from the herbs selected from *Terminalia chebula* and *Curcuma longa* for the prevention or treatment of liver damage caused by various factors such as viral hepatitis, cirrhosis, and liver damage from alcohol or drugs such as acetaminophen.

In another object, the invention provides a method of improving the liver health in humans or animals, wherein the method comprises supplementing the animals with an effective dose of a synergistic composition comprising at least one component selected from extract(s) and fraction(s) or mixtures thereof derived from *Sphaeranthus indicus* in combination with at least one component selected from extract(s) and fraction(s) or mixtures thereof derived from *Terminalia chebula*.

SUMMARY OF THE INVENTION

The present invention provides, novel synergistic compositions comprising at least one component selected from the extracts or fractions derived from *Sphaeranthus indicus* in combination with at least one component selected from the extracts or fractions derived from *Terminalia chebula* for improving the liver health. These synergistic compositions further contain optionally at least one additional biologically active components derived from plants, animals and microorganisms in association with pharmaceutically or nutraceutically acceptable actives, excipients, carriers or diluents.

In another aspect the invention provides methods of use of the synergistic compositions comprising at least one component selected from the extracts or fractions derived from *Sphaeranthus indicus* in combination with at least one component selected from the extracts or fractions derived from *Terminalia chebula* or mixtures thereof for improving the liver health.

In other aspect, the invention provides synergistic compositions comprising at least one component selected from the extracts or fractions derived from *Sphaeranthus indicus* in combination with at least one component selected from the extracts or fractions derived from *Terminalia chebula* for the prevention or treatment of liver damage caused by various factors such as viral hepatitis, cirrhosis, and liver damage from alcohol or drugs such as acetaminophen.

In a further aspect, the invention provides method of improving the liver health or treating liver damage in humans and animals caused by various factors such as viral hepatitis, cirrhosis, and liver damage from alcohol or drugs such as acetaminophen, wherein the method comprises supplementing the humans or animals with an effective dose of a synergistic composition comprising at least one component selected from the extracts or fractions derived from *Sphaeranthus indicus* in combination with at least one component selected from the extracts or fractions derived from *Terminalia chebula* or *Curcuma longa*.

DESCRIPTION OF THE FIGURES

FIGS. 2A and 2B.

FIGS. 3A, 3B, and 3C.

FIGS. 4A, 4B, and 4C: Liver cross section of Rohu fish.

DESCRIPTION OF THE INVENTION

The liver is a vital part of human/animal anatomy and it supports almost every other organ in the body. Because of its strategic location and multidimensional functions as the principal detoxifying organ and metabolic homeostasis maintaining organ, liver is prone to many disorders. Reactive Oxygen Species (ROS) are considered as the origin of numerous liver disorders, whose levels are known to be increased by exposure to certain drugs or chemicals, infections, external conditions, tissue injury etc. The Reactive Oxygen Species (ROS) play a crucial role in host defense against bacterial infections and controlled activation of many intracellular signaling pathways. Several differently localized and expressed enzymatic systems contribute to ROS formation in liver including endothelial NO synthases, cytochrome P450 monoxygenases and NADPH oxidase. Increased generation of ROS may cause aberrant stimulation of pathways leading to abnormal cell behavior. Antioxidant systems such as Glutathione, Superoxide dismutase and Catalase remove excess ROS to maintain the normal cell homeostasis. In chronic liver diseases there is increased ROS production, whereas the activity of antioxidant systems is decreased resulting in oxidative stress, a state commonly observed in people with alcohol abuse, hepatitis C infection, chronic cholestatis and liver fibrogenesis. The hepatic stellate cells, the major fibrogenic cell type in the liver produces a nonphagocytic form of NADPH, which modulate the fibrogenic function of the these cells and therefore the NADPH oxidase has been evolved as a potential target in the pathogenesis of hepatic fibrosis. Hence, the inventors have screened a vast number of herbal extracts for modulation of NADPH oxidase activity in a cellular model and found that the extracts of *Sphaeranthus indicus* flower heads (LN17131) and *Terminalia chebula* fruit (LN17129) showed potent NADPH oxidase inhibition activity as summarized in Table 1.

The inventors have randomly prepared several compositions comprising the extracts or fractions derived from *Sphaeranthus indicus* in combination with extracts or fractions derived from *Terminalia chebula* and tested their efficacy in inhibiting NADPH oxidase to identify compositions that show synergistic inhibition. It was found surprisingly that compositions comprising at least one component selected from the extracts or fractions derived from *Sphaeranthus indicus* in combination with at least one component selected from the extracts or fractions derived from *Terminalia chebula* showed more potent inhibition of NADPH oxidase when compared to the efficacy shown by the corresponding individual extracts derived from *Sphaeranthus indicus* and *Terminalia chebula*. The *S. indicus* flower heads enriched extract (LN17131) and *Terminalia chebula* fruit water extract (LN17129) for example showed 43.24% and 13.79% inhibition respectively at 125 ng/mL in HL-60 cells. The composition-2 (LN16013F2) containing these extracts at 1:1 ratio along with the excipients showed 71.62% inhibition at 250 ng/mL concentration, which is significantly better than the additive effect (43.24%+13.79%=57.03%) from these two ingredients, suggesting synergistic inhibition of NADPH by *S. indicus* flower head enriched extract (LN17131) and *Terminalia chebula* fruit extract (LN17129). These two ingredients also showed synergism when combined at other ratios, 1:2, 1:3 and 3:1 as shown by the improved NADPH oxidase inhibitory effects exhibited by the compositions-1, 3 and 4, (LN16013F1, LN16013F3 and LN16013F4) respectively. The results are summarized in Table 1.

The synergistic effects shown by these ingredients were further tested in in vivo models. For example, *Sphaeranthus indicus* flower heads enriched extract (LN17131) the composition (LN16013F2) comprising the *Sphaeranthus indicus* flower head enriched (LN17131) extract and *Terminalia chebula* water extract (LN17129); and *Terminalia chebula* water extract (LN17129) were supplemented to groups G3, G4 and G5 respectively. Oral treatment of G4 group animals with LN16013F2 at 200 mg/kg dose resulted in significantly lower levels of serum Alanine Aminotransferase (ALT) levels (129.17±20.18), when compared to the ALT levels observed in G3 group animals (255.83±41.12) treated with LN17131 and G5 group animals (275±133.9) treated with LN17129 at the same dose levels. Similarly, oral treatment with LN16013F2 (G4) at 200 mg/kg resulted in better reduction of serum Aspartate Aminotransferase (AST) levels (334.17±57.34), when compared to AST levels observed in LN17131 treated group (G3; 548.33±128.6) and LN17129 treated group (G5; 390.83±40.77). These results as summarized in Table 7 further confirm the synergistic efficacy of LN16013F2 in controlling hepatotoxicity by controlling $CCl_4$ induced liver enzyme levels. The decreased level of serum AST and ALT is a clear indication of the improvement of the functional status of the liver.

The water extract of *Sphaeranthus indicus* flower heads (LN17133) also showed similar synergistic efficacy when combined with the extracts derived from *Terminalia chebula*. For example, the *S. indicus* flower heads water extract (LN17133) and *Terminalia chebula* fruit water extract (LN17129) showed 21.47% and 45.29% inhibition NADPH oxidase respectively at 312.5 ng/mL in HL-60 cells. The composition-6 (LN16049F2) containing these extracts at 1:1 ratio showed 81.9% inhibition at 625 ng/mL concentration, which is significantly better than the additive effect (21.47%+45.29%=66.76%) from these two ingredients, suggesting synergistic inhibition of NADPH between water extracts of *S. indicus* flower head (LN17133) and *Terminalia chebula* fruit (LN17129). The other compositions composition-5, 7, 8 and 9 containing *S. indicus* flower head (LN17133) and *Terminalia chebula* fruit (LN17129) extracts at other ratios, such as 1:2 (LN16049F1), 2:1 (LN16049F3), 3:1 (LN16049F4) and 1:3 (LN16049F5) also showed synergism as shown by their improved NADPH oxidase inhibitory effects, when compared to the individual ingredient as summarized in Table 2.

Glutathione is an important antioxidant in humans and animals. Reduced form of glutathione (GSH) is very effective in preventing and ameliorating the damage to cellular components caused by ROS, peroxides, lipid peroxides hence glutathione (GSH) benefits liver health by combating oxidative stress caused to liver tissue following exposure to excess chemicals, pollutants, toxins, alcohol etc. Hence, the extracts and fractions derived from *Sphaeranthus indicus* and *Terminalia chebula* and their compositions were evaluated for their efficacy to increase GSH-levels in tert-butyl-hydroperoxide induced Hep G2 liver cells and the results are summarized in table 4.

The generation of reactive oxygen species (ROS) leads to oxidative stress and it plays an important role in the pathogenesis of many liver diseases. The attack of free radicals on poly unsaturated membrane lipid produces hydro peroxide (lipid peroxidation) which subsequently leads to the production of malondialdehyde (MDA). Increased production of MDA is known to correlate with elevated liver enzyme (AST and ALT) and as such MDA is marker for liver health. Hence the inventors have evaluated a few of the compositions for their synergistic inhibition against tert-butylhydroperoxide induced MDA in Hep G2 liver cells and the results are summarized in tables 5 and 6.

In addition to the data disclosed above, different compositions containing acetone or ethyl acetate or ethanol extracts of *Sphaeranthus indicus* flower heads in combination with water, hydro alcohol and acetone extracts of *Terminalia chebula*; and compositions containing ethanol, acetone, ethyl acetate or water extracts of *Sphaeranthus indicus* aerial parts in combination with water, hydro alcohol or acetone extracts of *Terminialia chebula* also showed synergistic inhibition of NADPH oxidase activity and/or MDA, and enhance the levels of reduced glutathione (GSH) levels as summarized in tables, 3A, 3B, 4, 5 and 6. The results thus suggest the observed synergism between these two herbs is independent of the solvent used for extraction.

Figure 1:
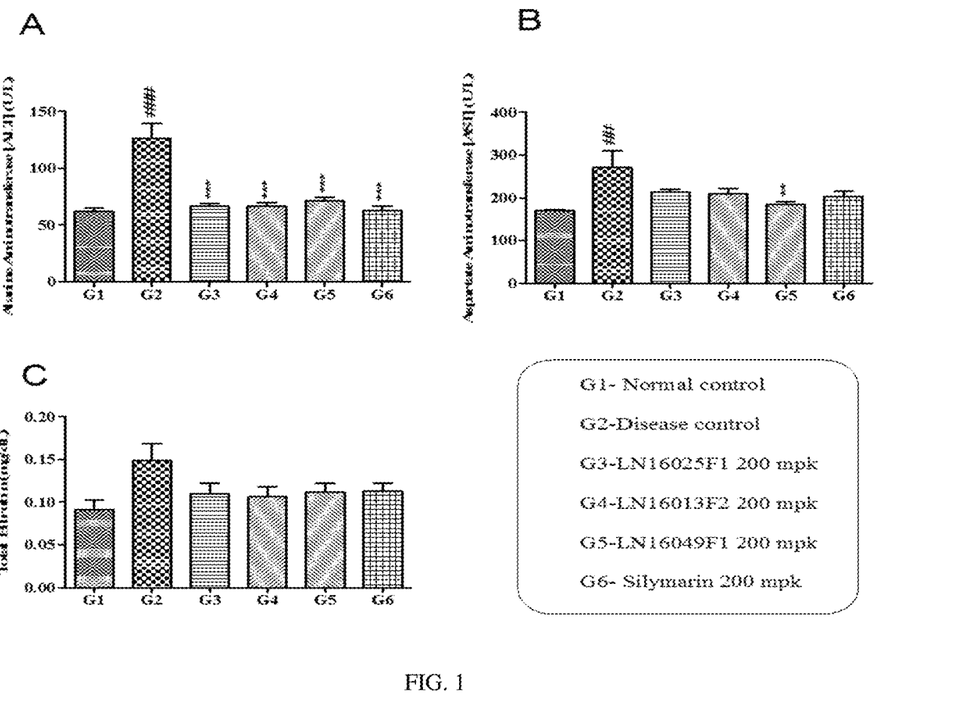
FIG. 1:—Effect of LN16025F1 (G3), LN16013F2 (G4) and LN16049F1 (G5) on ALT, AST and TB on day 15. Values are represented as Mean±S.E.M; n=6 animals per group. ###$P<0.001$, ##$P<0.01$ as compared to Vehicle control (G1), *$P<0.001$ and $P<0.01$ as compared to disease control (G2) group using one-way ANOVA followed by Dunnett's post-test.

The efficacy shown by composition-5 (LN16049F1), along with composition-2 (LN16013F2) and composition-10 (LN16025F1) in vitro, was further validated in vivo in acetaminophen induced liver damage model of rats. The study showed that acetaminophen markedly increased the activities of serum ALT and AST levels in disease control (G2) group as compared with the vehicle control group (G1). However, supplementation of LN16025F1, LN16013F2, LN16049F1 and silymarin to the animals of treatment groups G3, G4, G5 and G6 respectively significantly reduced serum ALT and AST on days 12 and 15. The data for day 15 is summarized in table 8 and FIG. 1. In addition, marked degree of centrilobular vacuolation/degeneration of hepatocytes and minimal to marked degree of pericapsular fibrous connective tissue proliferation mixed with adipocytes were evident in livers of Acetaminophen intoxicated rats from disease control group (G2) indicating induction of hepatotoxicity or hepatic damage. Microscopic examination of livers from G3, G4, G5 and G6 group animals, treated with LN16025F1, LN16013F2, LN16049F1 and Silymarin respectively did not reveal any vacuolation/degeneration of hepatocytes indicating potential ameliorative effects of these test items against Acetaminophen induced hepatic damage in rats. The degree of pericapsular fibrous connective tissue proliferation/adipocytes significantly reduced in livers of G3, G4 and G6 group animals, whereas such lesions were completely absent in livers of animals supplemented with LN16049F1 (G5).

Just like human Liver (Hepatic), Hepatopancreas in many aquatic animals is the central organ responsible for metabolism of food/feed consumed by animals. It does the functions of both liver and pancreas in aquatic animals, such as shrimp, fish, crabs etc. Liver health can be compromised under several disease conditions, which further leads to improper nutrition uptake, stunted growth and deterioration in overall health or death in severe cases. In aquatic animals, liver may be damaged due to infections or regular use of antibiotics or pesticides during the aqua culture. The farmers often use large doses of antibiotics and pesticides from the early stages during aquacultures, to improve the survival rate and prevent infections. The farmers also use harmful chemicals to control pond conditions. This leads to weakening of liver function and further affecting the GUT of the animal.

Figure 2A:
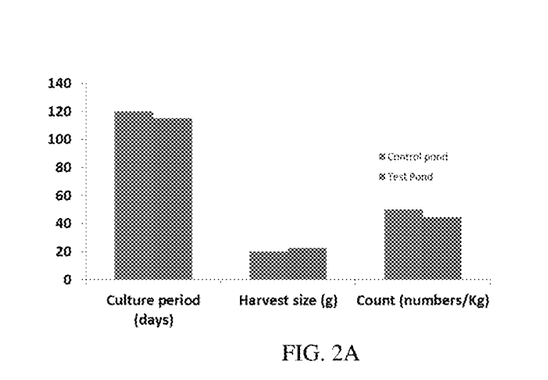
(FIG. 2A) Bar diagram shows reduction in culture period improvement in harvest size and shrimp count in culture pond supplemented with composition-34 at 2 g per kg feed/day in comparison to control pond.
Figure 2B:
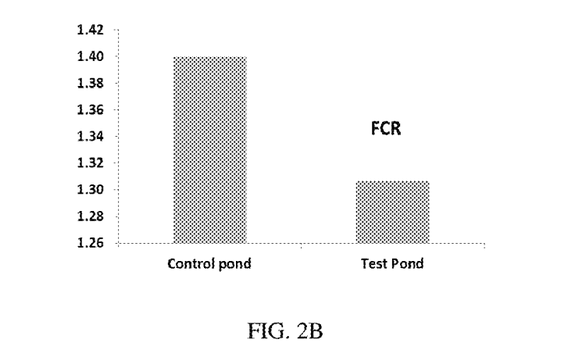
(FIG. 2B) Bar diagram shows effect of composition-34 on FCR (feed conversion ratio) Composition-34 supplementation at 2 g per kg feed/day showed improvement in FCR (Feed Conversion Ratio) compared to control pond.
Figure 3A:
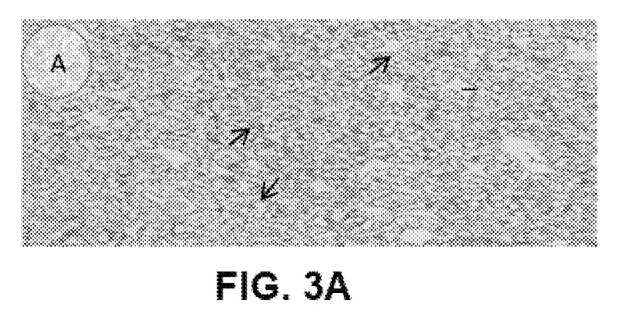
(FIG. 3A) Microphotograph of hepatopancreas of a shrimp infected with white gut disease showing extensive vacuolation/degeneration of inner epithelium of tubules and obstruction of lumen. H & E×200.
Figure 3B:
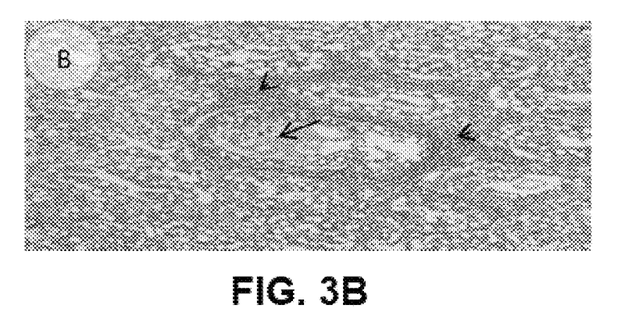
(FIG. 3B) Higher magnification of A showing extensive vacuolation/degeneration/necrosis of inner epithelium of hepatopancreatic tubules. Note the sloughing of microvilli into lumen (arrow) and causing obstruction and mononuclear cell infiltration (arrow head) in intertubular spaces. H & E×400.
Figure 3C:
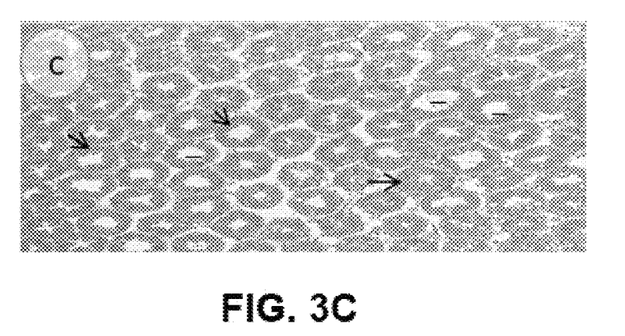
(FIG. 3C) Microphotograph of shrimp treated with composition-34, which shows numerous cross sections of tubules with normal intact inner epithelium (arrow) and lumen (L) H&E 200.

Hence the inventors have tested a few compositions of current invention in shrimp ponds and found surprisingly that the composition containing extract or fractions derived from *Sphaeranthus indicus* flower heads in combination with an extract derived from *Terminalia chebula*, optionally containing one or more of the herbal extracts derived from *Allium sativum, Andrographis paniculata* and *Ocimum sanctum, Curcuma longa Phyllanthus amarus, Silybum marianum* (milk thistle), *Tephrosia purpurea, Tinospora sinensis* improved the Hepatopancreatic health and increased the survival rate, reduction of culture time better nutrition uptake from the feed and improves Feed Conversion Ratio (FCR), growth and overall health. For example, composition-34 supplementation at 2 g per kg feed/day showed reduction in culture period by 5 days. Improvement in harvest size and count (shrimp numbers/kg) was also observed as shown in FIGS. 2A and 2B. Similarly composition-34 supplementation at 2 g per kg feed/day to the shrimps infected with white gut diseases (WGD) showed complete recovery from vacuolation/degeneration of inner epithelium of tubules and obstruction of lumen as shown in FIGS. 3A, 3B, and 3C.

Further the composition also has been shown to prevent various diseases associated with liver damage such as Acute hepatopancreatic necrosis disease (AHPND), White Gut disease, White feces syndrome, White spot Syndrome, disease due to Enterocytozoon hepatopenaei (EHP), Early mortality syndrome (EMS), Running mortality syndrome (RMS), Vibriosis, black gill disease, Muscle necrosis, White muscle disease, Muscle cramp syndrome, loose shell syndrome, TSV—Taura Syndrome Virus, YHV—Yellow Head Virus, IHHNV—Infectious Hypodermal and Hematopoietic Necrosis Virus etc. in shrimp and *columnaris*, gill disease, ick (ich), dropsy, tail and fin-rot, fungal infections, white spot disease, pop-eye, cloudy eye, swim bladder disease, lice and nematode worms infestation, water quality induced diseases, constipation, anorexia, chilodonella, ergasilus, tuberculosis, glugea, henneguya, hexamita, hole-in-the-head disease, injuries, leeches in aquaria, lymphocystis, marine velvet, neon-tetra disease, Infectious Salmon Anaemia (ISA), Infectious Hematopoietic Necrosis (IHN), Furunculosis, Bacterial Kidney Disease, helminth infection etc. in fish. In addition, supplementation of Composition-34 to fish feed completely reduced the bile pigment granules inside hepatocytes and inflammation at the periphery in Rohu fish as summarized in FIGS. 4A, 4B, and 4C. The foregoing results manifests that the compositions of the current invention are efficacious in protecting the hepatopancreas, improving the hepatopancreatic health or treating disease conditions associated with hepatopancreas in aquatic animals Therefore, in a preferred embodiment, the invention provides synergistic compositions comprising at least one component selected from the extracts, fractions or mixtures thereof derived from *Sphaeranthus indicus* in combination with at least one component selected from the extracts, fractions, active compound(s) or mixtures thereof derived from *Terminalia chebula* for protecting the liver, improving the liver health or treating disease conditions associated with liver in humans and animals.

In another embodiment, the invention provides synergistic composition(s) comprising at least one component selected from extracts, fractions or mixtures thereof derived *Sphaeranthus indicus* in combination with at least one component selected from the extract(s), fraction(s), active compound(s) or mixtures thereof derived from *Terminalia chebula* for protecting the liver, improving the liver health or treating disease conditions associated with liver in humans and animals, wherein, the synergistic compositions may contain optionally pharmaceutically or nutraceutically or dietically acceptable, excipients, carriers or diluents, wherein the pharmaceutically or dietetically acceptable excipients, carriers and diluents can be selected from glucose, fructose, sucrose, maltose, yellow dextrin, white dextrin, aerosil, microcrystalline cellulose, calcium stearate, magnesium stearate, sorbitol, stevioside, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, proteins, calcium salts, pigments, flavors, preservatives, distilled water, saline, aqueous glucose solution, alcohol, propylene glycol and polyethylene glycol, various animal and vegetable oils, white soft paraffin, paraffin, flavorants, colourants and wax.

In other embodiment, the invention provides synergistic composition(s) comprising at least one component selected from extracts, fractions or mixtures thereof derived from *Sphaeranthus indicus* in combination with at least one component selected from the extract(s), fraction(s), active compound(s) or mixtures thereof derived from *Terminalia chebula* for protecting the liver, improving the liver health or treating disease conditions associated with liver in humans and animals, where in the synergistic compositions further contain optionally at least one additional component selected from the group consisting of biologically active natural ingredients selected from the known anti-oxidants, anti-inflammatory agents, immunomodulating agents and the agents known for liver protection, improving liver health and treating liver diseases; pharmaceutically acceptable active ingredients, vitamins, minerals, wherein the agents known for liver protection, improving liver health and treating liver diseases are selected from extracts, fractions, pure phytochemicals or mixtures thereof derived from the plant raw materials of *Aegle marmelos, Allium sativum, Andrographis paniculata, Curcuma longa, Oscimum sanctum, Phyllanthus amarus, Silybum marianum* (milk thistle), *Tephrosia purpurea, Tinospora sinensis.*

In other embodiment, the invention provides synergistic composition(s) comprising at least one component selected from extracts, fractions or mixtures thereof derived from *Sphaeranthus indicus* in combination with at least one component selected from the extract(s), fraction(s), active compound(s) or mixtures thereof derived from *Terminalia chebula* for protecting the liver, improving the liver health or treating disease conditions associated with liver in humans and animals, wherein, the plant parts used in the present invention for the preparation of synergistic compositions are selected from the fruits, flower heads, flowers, rind, seed, leaves, stems, tender stems, bark, whole plant, aerial parts or mixtures thereof.

In other embodiment, the invention provides synergistic composition(s) comprising at least one component selected from extracts, fractions or mixtures thereof derived from *Sphaeranthus indicus* in combination with at least one component selected from the extract(s), fraction(s), active compound(s) or mixtures thereof derived from *Terminalia chebula* for protecting the liver, improving the liver health or treating disease conditions associated with liver in humans and animals, wherein solvents used for preparing the extracts and fractions can be selected from but not limited to C1-C5 alcohols, like ethanol, methanol, n-propanol, isopropyl alcohol; ketones like acetone, methylisobutyl ketone, chlorinated solvents like methylene dichloride and chloroform, water and mixtures thereof; C1-C7 hydrocarbons such as hexane; esters like ethyl acetate and the like and mixtures thereof.

In other embodiment, the invention provides synergistic composition(s) comprising at least one component selected from extracts, fractions or mixtures thereof derived from *Sphaeranthus indicus* in combination with at least one component selected from the extract(s), fraction(s), active compound(s) or mixtures thereof derived from *Terminalia chebula* for protecting the liver, improving the liver health or treating disease conditions associated with liver in humans and animals, wherein the compositions may be formulated into a dosage form selected from dry powder form, liquid form, beverage, food product, dietary supplement or any suitable form such as tablet, a capsule or a soft chewable or gummy bear.

In another embodiment, the invention provides synergistic composition(s) comprising at least one component selected from extracts, fractions or mixtures thereof derived from *Sphaeranthus indicus* in combination with at least one component selected from the extract(s), fraction(s), active compound(s) or mixtures thereof derived from *Terminalia chebula* for protecting the liver, improving the liver health or treating disease conditions associated with liver in humans and animals, wherein the composition(s) can be made into the dosage form of healthy foods, or food for specified health uses such as solid food like chocolate or nutritional bars, semisolid food like cream or jam, or gel and also beverage and the like, such as refreshing beverage, lactic acid bacteria beverage, drop, candy, chewing gum, gummy candy, yoghurt, ice cream, pudding, soft adzuki bean jelly, jelly, cookie, tea, soft drink, juice, milk, coffee, cereal, snack bar and the like.

In another embodiment, the invention provides synergistic composition(s) comprising at least one component selected from extracts, fractions or mixtures thereof derived from *Sphaeranthus indicus* in combination with at least one component selected from the extract(s), fraction(s), active compound(s) or mixtures thereof derived from *Terminalia chebula* for protecting the liver, improving the liver health or treating disease conditions associated with liver in humans and animals, wherein the weight of *Sphaeranthus indicus* derived component varies in the range of 10%-90% in the composition and the weight of *Terminalia chebula* derived component varies in the range of 90%-10%.

In another embodiment, the invention provides synergistic composition(s) comprising at least one component selected from extracts, fractions or mixtures thereof derived from *Sphaeranthus indicus* in combination with at least one component selected from the extract(s), fraction(s), active compound(s) or mixtures thereof derived from *Terminalia chebula* for protecting the liver, improving the liver health or treating disease conditions associated with liver in humans and animals, wherein, the *Sphaeranthus indicus* extract and fraction contains 7-hydroxyfrullanolide in the range of 12 to 30% in case of solvent extracts and 1 to 10% of total chlorogenic acids in case of water extracts as per HPLC method of analysis and the *Terminalia chebula* derived extract and fraction contain total polyphenols in the range of 20 to 80% as per spectrometric method of analysis, 1 to 6% total chebulagic acids and 1-12% total chebulinic acid, 1 to 10% ellagic acid and/or 1 to 10% gallic acid as per HPLC method of analysis.

In another embodiment, the invention provides the use of synergistic composition(s) comprising at least one component selected from extracts, fractions or mixtures thereof derived from *Sphaeranthus indicus* in combination with at least one component selected from the extract(s), fraction(s), active compound(s) or mixtures thereof derived from *Terminalia chebula* for protecting the liver, improving the liver health or treating disease conditions associated with liver in humans and animals.

In yet another embodiment, the invention provides method(s) of protecting the liver, improving the liver health or treating at least one disease conditions associated with liver in humans and animals, which include viral hepatitis, cirrhosis, non-alcoholic fatty liver disease (NAFLD), and liver damage from alcohol or drugs such as acetaminophen, elevated levels of Alanine transaminase (ALT), Aspartate transaminase (AST), alkaline phosphatase (ALP), bilirubin, triglycerides (TG), Gammaglutaryl tranferase, wherein the method comprises supplementing the humans and animals with an effective dose of the synergistic composition comprising at least one component selected from extracts, fractions or mixtures thereof derived from *Sphaeranthus indicus* in combination with at least one component selected from the extract(s), fraction(s), active compound(s) or mixtures thereof derived from *Terminalia chebula*.

In other embodiment, the invention provides method(s) of protecting the liver, improving the liver health or treating at least one disease conditions associated with liver in humans and animals, which include viral hepatitis, cirrhosis, non-alcoholic fatty liver disease (NAFLD) and liver damage from alcohol or drugs such as acetaminophen, elevated levels of Alanine transaminase (ALT), Aspartate transaminase (AST), alkaline phosphatase (ALP), bilirubin, triglycerides (TG), Gammaglutaryl tranferase, wherein the method comprises supplementing the humans and animals with an effective dose of the synergistic composition comprising at least one component selected from extracts, fractions or mixtures thereof derived from *Sphaeranthus indicus* in combination with at least one component selected from the extract(s), fraction(s), active compound(s) or mixtures thereof derived from *Terminalia chebula*, which contain optionally at least one additional component selected from the group consisting of biologically active natural ingredients selected from the known anti-oxidants, anti-inflammatory agents, immunomodulating agents and the agents known for liver protection, improving liver health and treating liver diseases; pharmaceutically acceptable active ingredients, vitamins, minerals, pharmaceutically or nutraceutically or dietically acceptable actives, excipients, carriers or diluents, or mixtures thereof, wherein the agents known for liver protection, improving liver health and treating liver diseases are selected from extracts, fractions, pure phytochemicals or mixtures thereof derived from the plant raw materials of *Aegle marmelos, Allium sativum, Andrographis paniculata, Curcuma longa, Oscimum sanctum, Phyllanthus amarus, Silybum marianum* (milk thistle), *Tephrosia purpurea, Tinospora sinensis*.

In another embodiment, the invention provides method(s) of protecting the liver, improving the liver health or treating at least one disease conditions associated with liver in humans and animals, wherein the animals are selected from terrestrial and aquatic species, wherein the method comprises supplementing the animal with an effective dose of the synergistic composition comprising at least one component selected from extracts, fractions or mixtures thereof derived from *Sphaeranthus indicus* in combination with at least one component selected from the extract(s), fraction(s), active compound(s) or mixtures thereof derived from *Terminalia chebula*, which contain optionally at least one additional component selected from the group consisting of biologically active natural ingredients selected from the known anti-oxidants, anti-inflammatory agents, immunomodulating agents and the agents known for liver protection, improving liver health and treating liver diseases; pharmaceutically acceptable active ingredients, vitamins, minerals, pharmaceutically or nutraceutically or dietically acceptable actives, excipients, carriers or diluents, or mixtures thereof, wherein the agents known for liver protection, improving liver health and treating liver diseases are selected from extracts, fractions, pure phytochemicals or mixtures thereof derived from the plant raw materials of *Aegle marmelos, Allium sativum, Andrographis paniculata, Curcuma longa, Oscimum sanctum, Phyllanthus amarus, Silybum marianum* (milk thistle), *Tephrosia purpurea, Tinospora sinensis*.

In another embodiment, the invention provides method(s) of protecting the liver, improving the liver health or treating at least one disease conditions associated with liver in animals, wherein the liver related diseases of aquatic species are selected from Acute hepatopancreatic necrosis disease (AHPND), White Gut disease, White feces syndrome, White spot Syndrome, disease due to Enterocytozoon hepatopenaei (EHP), Early mortality syndrome (EMS), Running mortality syndrome (RMS), Vibriosis, black gill disease, Muscle necrosis, White muscle disease, Muscle cramp syndrome, loose shell syndrome, TSV—Taura Syndrome Virus, YHV—Yellow Head Virus, IHHNV—Infectious Hypodermal and Hematopoietic Necrosis Virus etc. in shrimp and *columnaris*, gill disease, ick (ich), dropsy, tail and fin-rot, fungal infections, white spot disease, pop-eye, cloudy eye, swim bladder disease, lice and nematode worms infestation, water quality induced diseases, constipation, anorexia, chilodonella, ergasilus, tuberculosis, glugea, henneguya, hexamita, hole-in-the-head disease, injuries, leeches in aquaria, lymphocystis, marine velvet, neon-tetra disease, Infectious Salmon Anaemia (ISA), Infectious Hematopoietic Necrosis (IHN), Furunculosis, Bacterial Kidney Disease, helminth infection, wherein the method comprises supplementing the mammal with an effective dose of the synergistic composition comprising at least one component selected from extracts, fractions or mixtures thereof derived from *Sphaeranthus indicus* in combination with at least one component selected from the extract(s), fraction(s), active compound(s) or mixtures thereof derived from *Terminalia chebula*, which contain optionally at least one additional component selected from the group consisting of biologically active natural ingredients selected from the known anti-oxidants, anti-inflammatory agents, immunomodulating agents and the agents known for liver protection, improving liver health and treating liver diseases; pharmaceutically acceptable active ingredients, vitamins, minerals, pharmaceutically or nutraceutically or dietically acceptable actives, excipients, carriers or diluents, or mixtures thereof, wherein the agents known for liver protection, improving liver health and treating liver diseases are selected from extracts, fractions, pure phytochemicals or mixtures thereof derived from the plant raw materials of *Aegle marmelos, Allium sativum, Andrographis paniculata, Curcuma longa, Oscimum sanctum, Phyllanthus amarus, Silybum marianum* (milk thistle), *Tephrosia purpurea, Tinospora sinensis*.

The following examples, which include preferred embodiments, will serve to illustrate the practice of this invention, it being understood that the particulars shown are by way of example and for purpose of illustrative discussion of preferred embodiments of the invention.

Example 1

A) Preparation of *Sphaeranthus indicus* Flower Heads Enriched Extract (LN17131) Extract:

Dried flower heads of *Sphaeranthus indicus* (1 Kg) was pulverized to coarse powder and extracted with ethyl alcohol (5 L) for 2 h at ambient temperature. The extraction was repeated thrice (3×3 L) under similar temperature conditions. The extracts were combined, the combined extract was fine filtered, and the clear solution was evaporated under reduced pressure to obtain syrupy liquid. Then water (500 mL) was added to the concentrate and the contents were mixed well. The mixture was extracted with EtOAc (4×500 ml). The combined EtOAc extractives were concentrated under vacuum to give residue of ethyl acetate extract fraction (50 g) containing 20.6% 7-hydroxyfrullanolide. The aqueous layer was concentrated separately under reduced pressure to give a residue aqueous extract fraction (80 g). The ethyl acetate extract fraction and aqueous extract fractions were combined at 3:1 ratio to obtain *Sphaeranthus indicus* flower heads enriched extract (LN17131) containing 15.2% 7-hydroxyfrullanolide. Alternatively, these two extracts can be combined at any desired ratio so as to maintain a required concentration of active or phytochemical marker.

B) Preparation of *Sphaeranthus indicus* Flower Heads Water Extracts (LN17133).

Dried flower heads of *Sphaeranthus indicus* (100 g) was pulverized and the powder was extracted with water (700 mL) using continuous percolation process at ambient temperature for 1.5 h in a soxhlet apparatus. The extract was removed from Soxhlet and the spent raw material was re-extracted twice with water (2×500 mL) under similar conditions. The extracts were combined, fine filtered and the filtrate was concentrated on a rotary evaporator under vacuum at 40 50° C. to obtain water extract of *Sphaeranthus indicus* flower heads as a brown residue (LN17133, 17.2 g), which contains 3.35% of total chlorogenic acids (di-caffeoylquinic acid & 5-O-caffeoylquinic acid) as per HPLC method of analysis.

C) Preparation of *Sphaeranthus indicus* Flower Heads Acetone Extract (LN17122) and Ethyl Acetate Extract (LN17123):

The raw material of 100 g of *Sphaeranthus indicus* flower heads was pulverized and the powder extracted with acetone (600 mL) using continuous percolation at ambient temperature for 1.5 h in soxhlet apparatus. The extract was removed from Soxhlet and the spent raw material was re-extracted twice with acetone (2×300 mL) under similar conditions. The combined extract was fine filtered and concentrated on a rotary evaporator to obtain the acetone extract of *Sphaeranthus indicus* flower heads (LNLN17122; 8 g) containing 13.7% 7-hydroxyfrullanolide. Same extraction procedure was repeated with ethyl acetate as the extraction solvent on 100 g of *Sphaeranthus indicus* flower heads to obtain ethyl acetate extract (LN17123; 9.3 g, 30.2% 7-hydroxyfrullanolide) of *Sphaeranthus indicus* flower heads.

D) Preparation of *Sphaeranthus indicus* Flower Heads Ethanol Extract (LN17121).

Dried flower heads of *Sphaeranthus indicus* (1 Kg) was pulverized to coarse powder and extracted with ethyl alcohol (6 L) for 2 h at 40-45° C. The extract was filtered and the residue was subjected to extraction process thrice (3×4 L) under similar temperature conditions. The extracts were combined, the combined extract was fine filtered, and the clear extract was evaporated under reduced pressure to remove alcohol completely to obtain *Sphaeranthus indicus* flower heads ethanol extract (LN17121; 120 g, 12% 7-hydroxyfrullanolide).

Example 2

A) Preparation of *Sphaeranthus indicus* Aerial Parts Ethanol Extracts (LN17124).

Dried aerial parts of *Sphaeranthus indicus* (1 Kg) was pulverized to coarse powder and extracted with commercial ethyl alcohol (6 L) for 2 h at 55-60° C. The extract was filtered and the residue was subjected to extraction process thrice (3×4 L) under similar temperature conditions. The extracts were combined, the combined extract was fine filtered, and the clear extract was evaporated under reduced pressure to remove alcohol completely to obtain *Sphaeranthus indicus* aerial parts extract (LN17124; 95 g).

B) Preparation of Acetone (LN17125) and Ethyl Acetate (LN17126) Extracts of *Sphaeranthus indicus* Aerial Parts:

The raw material of 100 g of *Sphaeranthus indicus* aerial parts was pulverized and the powder extracted with acetone (600 mL) using continuous percolation at ambient temperature for 1.5 h in soxhlet apparatus. The extract was removed from Soxhlet and the spent raw material was re-extracted twice with acetone (2×300 mL) under similar conditions. The combined extract was fine filtered and concentrated on a rotary evaporator to obtain the acetone extract of *Sphaeranthus indicus* aerial parts (LN17125; 12 g, 13.4% 7-hydroxyfrullanolide). Same extraction procedure was repeated with ethyl acetate as the extraction solvent on 100 g of *Sphaeranthus indicus* aerial parts to obtain ethyl acetate extract (LN17126; 8 g, 14.9% 7-hydroxyfrullanolide) of *Sphaeranthus indicus* aerial parts.

C) Preparation of *Sphaeranthus indicus* Aerial Parts Water Extracts (LN17134).

Dried flower heads of *Sphaeranthus indicus* (100 g) was pulverized and the powder was extracted with water (700 mL) using continuous percolation process at ambient temperature for 1.5 h in a soxhlet apparatus. The extract was removed from Soxhlet and the spent raw material was re-extracted twice with ethanol (2×500 mL) under similar conditions. The extracts were combined, fine filtered and the filtrate concentrated on a rotary evaporator under vacuum at ambient temperature to obtain water extract (LN17134) of *Sphaeranthus indicus* aerial parts as a brown residue (17.54 g).

D) Preparation of *Sphaeranthus indicus* Aerial Parts Enriched Extract (LN17132) Extract:

Dried aerial parts of *Sphaeranthus indicus* (1 Kg) was pulverized to coarse and extracted with ethyl alcohol (5 L) for 2 h at ambient temperature. The extraction was repeated thrice (3×3 L) under similar temperature conditions. The extracts were combined, the combined extract was fine filtered, and the clear solution was evaporated under reduced pressure to remove most of the alcohol. Then water (500 mL) was added to the concentrate and the contents were mixed well. The mixture was extracted with EtOAc (4×500 ml). The combined EtOAc extractives were concentrated under vacuum to give residue of ethyl acetate extract fraction (65 g). The aqueous layer was concentrated under reduced pressure to give a residue aqueous extract fraction (70 g). The ethyl acetate extract fraction and aqueous extract fractions were combined at 3:1 ratio to obtain *Sphaeranthus indicus* aerial parts extract (LN17132).

Example 3

A) Preparation of *Terminalia chebula* Water Extracts (LN17129).

Dried fruits of the plant material *Terminallia chebula* (1 Kg) were pulverized to coarse powder and extracted with water (6 L) at 65-70° C. for 2 hr. The extract was separated from the raw material by filtration. Extraction process was repeated thrice on the residue using 4.5 L of water each time under similar extraction conditions. All the extracts were combined, the combined extract was fine filtered, and the clear extract was evaporated on a climbing film evaporator at 50-60° C. and the concentrate was dried in vacuum dryer to obtain water extract of *Terminalia chebula* (LN17129) as a powder residue (370 g).

B) Preparation of *Terminalia chebula* Acetone Extract (LN17127).

Dried fruits of the plant material *Terminallia chebula* (250 g) was pulverized to coarse powder, extracted with acetone (4 L) at ambient temperature for 2 hr. The extraction was repeated thrice (3×3 L) under similar extraction conditions. The extracts were combined, the combined extracts were fine filtered, and the clear extract was evaporated under reduced pressure to completely remove acetone and dried under reduced pressure to obtain *Terminalia chebula* acetone extract (LN17127) as dry powder residue (50.0 g).

C) Preparation of *Terminalia chebula* Hydro Alcohol Extract (LN17128).

Dried fruits of the plant material *Terminallia chebula* (250 g) was pulverized to coarse powder, extracted with 50% ethanol (4 L) at ambient temperature for 2 hr. Extraction process was repeated thrice (3×3 L) under similar extraction conditions. The extracts were combined, the combined extracts were fine filtered, and the clear extract was evaporated to dryness on a rotavapour to completely remove solvent and dried under vacuum to obtain *Terminalia chebula* hydroalcohol extract (LN17128) as dry powder (65.0 g).

The *Allium sativum* water extract and *Ocimum sanctum* water extract used in the studies were procured from Chemiloids Life Sciences, Pvt. Ltd., Vijayawada Example 4

Compositions Containing *Sphaeranthus indicus* Extracts and *Terminalia chebula* Extracts Composition-1 (LN16013F1):

Composition-1 (LN16013F1) is prepared by mixing *Sphaeranthus indicus* flower heads enriched extract (LN17131) and *Terminalia chebula* water extract (LN17129) in the ratio of 1:2 along with the excipients as shown below.

| | |
|---|---|
| LN17131 | 20% |
| LN17129 | 40% |
| MCCP | 33% |
| Neusiline | 5% |
| Syloid 244FP | 2% |

Composition-2 (LN16013F2):

Composition-2 (LN16013F2) is prepared by mixing *Sphaeranthus indicus* flower heads enriched extract (LN17131) and *Terminalia chebula* water extract (LN17129) in the ratio of 1:1 along with the excipients as shown below.

| | |
|---|---|
| LN17131 | 30% |
| LN17129 | 30% |
| MCCP | 33% |
| Neusiline | 5% |
| Syloid 244FP | 2% |

Composition-3 (LN16013F3):
Composition-3 (LN16013F3) is prepared by mixing *Sphaeranthus indicus* flower heads enriched extract (LN17131) and *Terminalia chebula* water extract (LN17129) in the ratio of 1:3.

Composition-4 (LN16013F4):
Composition-4 (LN16013F4) is prepared by mixing *Sphaeranthus indicus* flower heads enriched extract (LN17131) and *Terminalia chebula* water extract (LN17129) in the ratio of 3:1.

Composition-5 (LN16049F1):
Composition-5 (LN16049F1) is prepared by mixing *Sphaeranthus indicus* flower heads water extract (LN17133) and *Terminalia chebula* water extract (LN17129) in the ratio of 1:2.

Composition-6 (LN16049F2):
Composition-6 (LN16049F2) is prepared by mixing *Sphaeranthus indicus* flower heads water extract (LN17133) and *Terminalia chebula* water extract (LN17129) in the ratio of 1:1.

Composition-7 (LN16049F3):
Composition-7 (LN16049F3) is prepared by mixing *Sphaeranthus indicus* flower heads water extract (LN17133) and *Terminalia chebula* water extract (LN17129) in the ratio of 2:1.

Composition-8 (LN16049F4):
Composition-8 (LN16049F4) is prepared by mixing *Sphaeranthus indicus* flower heads water extract (LN17133) and *Terminalia chebula* water extract (LN17129) in the ratio of 3:1.

Composition-9 (LN16049F5):
Composition-9 (LN16049F5) is prepared by mixing *Sphaeranthus indicus* flower heads water extract (LN17133) and *Terminalia chebula* water extract (LN17129) in the ratio of 1:3.

Composition-10 (LN16025F1):
Composition-10 (LN16025F1) is prepared by mixing *Sphaeranthus indicus* aerial parts water extract (LN17134) and *Terminalia chebula* water extract (LN17129) in the ratio of 2:1.

Composition-11 (LN16025F2):
Composition-11 (LN16025F2) is prepared by mixing *Sphaeranthus indicus* aerial parts water extract (LN17134) and *Terminalia chebula* water extract (LN17129) in the ratio of 1:1.

Composition-12 (LN16014F1):
Composition-12 (LN16014F1) is prepared by mixing *Sphaeranthus indicus* aerial parts enriched extract (LN17132) and *Terminalia chebula* water extract (LN17129) in the ratio of 1:2.

Composition-13 (LN16014F2):
Composition-13 (LN16014F2) is prepared by mixing *Sphaeranthus indicus* aerial parts enriched extract (LN17132) and *Terminalia chebula* water extract (LN17129) in the ratio of 1:1.

Composition-14 (LN16014F3):
Composition-14 (LN16014F3) is prepared by mixing *Sphaeranthus indicus* aerial parts enriched extract (LN17132) and *Terminalia chebula* water extract (LN17129) in the ratio of 1:3.

Composition-15:
Composition-15 is prepared by mixing *Sphaeranthus indicus* flower heads direct ethanol extract (LN17121) and *Terminalia chebula* water extract (LN17129) in the ratio of 1:2.

Composition-16:
Composition-16 is prepared by mixing *Sphaeranthus indicus* flower heads direct ethanol extract (LN17121) and *Terminalia chebula* water extract (LN17129) in the ratio of 1:1.

Composition-17:
Composition-17 is prepared by mixing *Sphaeranthus indicus* flower heads direct ethanol extract (LN17121) and *Terminalia chebula* water extract (LN17129) in the ratio of 2:1.

Composition-18:
Composition-18 is prepared by mixing *Sphaeranthus indicus* flower heads direct ethanol extract (LN17121) and *Terminalia chebula* fruit hydro alcohol extract (LN17128) in the ratio of 1:1.

Composition-19:
Composition-19 is prepared by mixing *Sphaeranthus indicus* flower heads acetone extract (LN17122) and *Terminalia chebula* fruit water extract (LN17129) in the ratio of 1:1.

Composition-20:
Composition-20 is prepared by mixing *Sphaeranthus indicus* flower heads acetone extract (LN17122) and *Terminalia chebula* fruit acetone extract (LN17127) in the ratio of 1:1.

Composition-21:
Composition-21 is prepared by mixing *Sphaeranthus indicus* flower heads acetone extract (LN17122) and *Terminalia chebula* fruit hydro alcohol extract (LN17128) in the ratio of 1:1.

Composition-22:
Composition-22 is prepared by mixing *Sphaeranthus indicus* flower heads ethyl acetate extract (LN17123) and *Terminalia chebula* water extract (LN17129) in the ratio of 1:2.

Composition-23:
Composition-23 is prepared by mixing *Sphaeranthus indicus* flower heads ethyl acetate extract (LN17123) and *Terminalia chebula* water extract (LN17129) in the ratio of 1:1.

Composition-24:
Composition-24 is prepared by mixing *Sphaeranthus indicus* flower heads ethyl acetate extract (LN17123) and *Terminalia chebula* water extract (LN17129) in the ratio of 2:1.

Composition-25:
Composition-25 is prepared by mixing *Sphaeranthus indicus* flower heads ethyl acetate extract (LN17123) and *Terminalia chebula* hydro alcohol extract (LN17128) in the ratio of 1:1.

Composition-26:
Composition-26 is prepared by mixing *Sphaeranthus indicus* aerial parts extract (LN17132) and *Terminalia chebula* acetone extract (LN17127) in the ratio of 1:1.

Composition-27:

Composition-27 is prepared by mixing *Sphaeranthus indicus* aerial parts enriched extract (LN17132) and *Terminalia chebula* hydro alcohol extract (LN17128) in the ratio of 1:1.

Composition-28:

Composition-28 is prepared by mixing *Sphaeranthus indicus* aerial parts direct ethanol extract (LN17124) and *Terminalia chebula* water extract (LN17129) in the ratio of 1:2.

Composition-29:

Composition-29 is prepared by mixing *Sphaeranthus indicus* aerial parts direct ethanol extract (LN17124) and *Terminalia chebula* water extract (LN17129) in the ratio of 1:1.

Composition-30:

Composition-30 is prepared by mixing *Sphaeranthus indicus* aerial parts direct ethanol extract (LN17124) and *Terminalia chebula* water extract (LN17129) in the ratio of 2:1.

Composition-31:

Composition-31 is prepared by mixing *Sphaeranthus indicus* aerial ethanol extract (LN17124) and *Terminalia chebula* hydro alcohol extract (LN17128) in the ratio of 1:1.

Composition-32:

Composition-32 is prepared by mixing *Sphaeranthus indicus* aerial parts acetone extract (LN17125) and *Terminalia chebula* water extract (LN17129) in the ratio of 1:1.

Composition-33:

Composition-33 is prepared by mixing *Sphaeranthus indicus* aerial parts ethyl acetate extract (LN17126) and *Terminalia chebula* water extract (LN17129) in the ratio of 1:1.

Composition-34:—

Composition-34 prepared by mixing *Sphaeranthus indicus* flower head enriched extract (LN17131), *Terminalia chebula* water extract (LN17129) and *Allium sativum* (Garlic) water extract in 1:4:5 ratio.

Composition-35:—

Composition-35 prepared by mixing *Sphaeranthus indicus* flower head enriched extract (LN17131), *Terminalia chebula* water extract (LN17129) and *Ocimum sanctum* water extract in 1:4:5 ratio.

Example 5

Efficacy of *Sphaeranthus indicus* enriched extract (LN17131), *Terminalia chebula* water extract (LN17129) and their compositions-1 to 4 (LN16013F1 to F4) in inhibiting NADPH Oxidase activity in in HL-60 cellular model. HL-60 cells were suspended in HBSS @ 1 million/ml (5 ml cell suspension prepared for one 96-well plate) in presence of 20 mM L-012 (a luminol based chemiluminescent probe). Prepared required samples and control stocks with 0.8% DMSO in Reaction Buffer. Added 50 µl cell suspension per well of a White opaque 96 well plate. Added 25 µl test samples (0.2% final DMSO conc.) per well. Immediately started reading the plate in luminescence mode, at 37° C. for 20 mins at two minutes interval. After 20 minutes added 25 µl of 400 nM PMA (phorbol 12-myristate 13-acetate) (final concentration 100 nM) to all the wells except non-induction or blank wells. Read the plate in luminescence mode, at 37° C. for 20 mins at two minutes interval. Calculated Area Under Curve (AUC) for each treatment and determined the percentage inhibition of NADPH oxydase using the formula. Percentage inhibition=(AUC of Normalized induction–AUC in Normalized treatments)×100/AUC of Normalized induction. The results are summarized in Table 1.

TABLE 1

| | LN17131 | | LN17129 | | | % inhibition of NADPH Oxidase activity | |
|---|---|---|---|---|---|---|---|
| Composition # | ng/mL | % inhibition | ng/mL | % inhibition | Ratio | Additive (calculated) | Observed at 250 ng |
| LN16013F1 | 83.33 | 9.19% | 166.67 | 57.66% | 1:2 | 66.85% | 82.14% |
| LN16013F2 | 125.00 | 13.79% | 125.00 | 43.24% | 1:1 | 57.03% | 71.62% |
| LN16013F3 | 62.50 | 6.81% | 187.50 | 64.87% | 1:3 | 71.76% | 84.82% |
| LN16013F4 | 187.5 | 20.69 | 62.50 | 21.62 | 3:1 | 42.31% | 76.84% |

Using the same procedure, the data obtained for *Sphaeranthus indicus* water extract (LN17133), *Terminalia chebula* water extract (LN17129) and their compositions-5 to 9 (LN16049F1 to F5) is summarized in Table 2.

TABLE 2

| | LN17133 | | LN17129 | | | % Inhibition of NADPH Oxidase activity | |
|---|---|---|---|---|---|---|---|
| Composition # | µg/mL | % inhibition | µg/mL | % inhibition | Ratio | Additive (Calculated) | Observed at 625 ng/ml |
| LN16049F4 | 468.75 | 32.20 | 156.25 | 22.64 | 3:1 | 54.84 | 70.61 |
| LN16049F3 | 416.66 | 28.62 | 208.34 | 30.24 | 2:1 | 58.86 | 76 |
| LN16049F2 | 312.5 | 21.47 | 312.5 | 45.29 | 1:1 | 66.76 | 81.9 |
| LN16049F1 | 208.34 | 14.31 | 416.66 | 60.39 | 1:2 | 74.7 | 84.71 |
| LN16049F5 | 156.25 | 10.73 | 468.75 | 67.94 | 1:3 | 78.67 | 90.43 |

Using the same procedure, the data obtained for different extracts of *Sphaeranthus indicus* and *Terminalia chebula*, and their compositions is summarized below in Tables 3A and 3B.

TABLE 3A

| | | | | | | | % inhibition of NADPH oxidase activity | |
|---|---|---|---|---|---|---|---|---|
| | dose | LN17121 | | LN17129 | | | Additive | |
| Composition # | (ng/ml) | ng/mL | % inhibition | ng/mL | % inhibition | Ratio | (Calculated) | Observed |
| Composition-15 | 100 | 33.34 | 3.46 | 66.66 | 37.7 | 1:2 | 41.16 | 52.64 |
| Composition-16 | 100 | 50 | 5.2 | 50 | 28.30 | 1:1 | 33.5 | 41.45 |
| Composition-17 | 100 | 66.66 | 6.92 | 33.34 | 18.87 | 2:1 | 25.79 | 36.79 |
| | | LN17121 | | LN17128 | | | | |
| Composition-18 | 100 | 50 | 5.2 | 50 | 24.82 | 1:1 | 30.02 | 44.77 |
| | | LN17122 | | LN17129 | | | | |
| Composition-19 | 100 | 50 | 18.89 | 50 | 35.63 | 1:1 | 54.52 | 67.62 |
| | | LN17122 | | LN17127 | | | | |
| Composition-20 | 3.7 | 1.85 | 2.31 | 1.85 | 2.77 | 1:1 | 5.08 | 26.92 |

TABLE 3B

| | | | | | | | % inhibition of NADPH oxidase activity | |
|---|---|---|---|---|---|---|---|---|
| | dose | LN17122 | | LN17128 | | | Additive | |
| Composition # | (ng/ml) | ng/mL | % inhibition | ng/mL | % inhibition | Ratio | (Calculated) | Observed |
| Composition-21 | 3.7 | 1.85 | 2.31 | 1.85 | 4.57 | 1:1 | 6.88 | 33.81 |
| | | LN17123 | | LN17129 | | | | |
| Composition-22 | 33.3 | 11.1 | 3.22 | 22.2 | 4.02 | 1:2 | 7.24 | 19.67 |
| | | LN17123 | | LN17128 | | | | |
| Composition-25 | 100 | 50 | 7.27 | 50 | 31.64 | 1:1 | 38.91 | 53.94 |
| | | LN17132 | | LN17127 | | | | |
| Composition-26 | 3.7 | 1.85 | 1.90 | 1.85 | 2.82 | 1:1 | 4.72 | 39.84 |
| | | LN17132 | | LN17128 | | | | |
| Composition-27 | 11.1 | 5.55 | 1.04 | 5.55 | 2.39 | 1:1 | 3.43 | 11.17 |
| | | LN17124 | | LN17129 | | | | |
| Composition-28 | 33.3 | 11.1 | 4.53 | 22.2 | 14.54 | 1:2 | 19.07 | 53.66 |
| Composition-29 | 33.3 | 16.65 | 6.8 | 16.65 | 10.90 | 1:1 | 17.7 | 45.66 |
| Composition-30 | 33.3 | 22.2 | 9.06 | 11.1 | 7.27 | 2:1 | 16.33 | 29.47 |
| | | LN17125 | | LN17129 | | | | |
| Composition-32 | 100 | 50 | 1.36 | 50 | 20.75 | 1:1 | 22.11 | 45.63 |

Example 6

Efficacy of *Sphaeranthus indicus* Extracts, *Terminalia chebula* Extracts and their Compositions for Increase in Reduced Form of Glutathione:

HepG2 cells ($0.5 \times 10^6$ cells/well) were seeded in a 24-well cell culture plate containing 500 μL of α-MEM+10% FBS and incubated overnight at 37° C. in a $CO_2$ incubator. Next day, cells were serum starved for 24 hours by replacing the medium with 400 μL of RPMI. On the following day, fresh RPMI+10% FBS medium was added and pre-treated with 50 μL of respective concentrations of test samples for 1 hour. Cells receiving 0.2% DMSO were considered as vehicle controls. Except vehicle controls, all the wells were induced with 50 μL tert-Butyl hydroperoxide (t-BHP) to achieve final concentration of 500 μM and incubated for 4 hours at 37° C. in a $CO_2$ incubator. Supernatants were discarded and cells were scraped with 100 μL 5% sulfosalicylic acid (SSA). Samples were freeze-thawed for 3 times and centrifuged at 8000×g for 5 minutes at 4° C. Then, 20 μL of samples/standards were added to the respective wells of a 96-well plate and subsequently 50 μL of DTNB reagent was added and absorbance was measured at 412 nm in SpectramaxM2e spectrophotometer. The results are summarized below in Table 4.

Glutathione (%) was calculated using the following formula:

$$\% \text{ Reduced Glutathione } (GSH) = \frac{\mu g \text{ of } GSH \text{ in treated} \times 100}{\mu g \text{ of } GSH \text{ in un-induced Vehicle Control}}$$

Note- μg of GSH normalization was done by using μg/ml values from standard graph to μg/$10^5$ cells.

Example 7

Efficacy of *Sphaeranthus indicus* Extracts, *Terminalia chebula* Extracts and their Compositions for Inhibition of Malondialdehyde (MDA).

In a six well cell culture plate, two million HepG2 cells were seeded in each well containing 2 mL of MEM medium (with 10% fetal bovine serum, FBS) and incubated overnight at 37° C. in a $CO_2$ incubator. After washing with 2 mL of RPMI (no serum) medium, cells were replaced with 1.3 mL of RPMI+10% FBS and pre-treated with respective concentrations of test samples for one hour. Cells receiving 0.2% DMSO were considered as vehicle controls. Except vehicle controls, all the wells were induced with 500 μl tert-Butyl hydroperoxide (t-BHP) to achieve the final concentration of 300 μM. After 4 hours of incubation at 37° C. in a $CO_2$ incubator, supernatants were collected into tubes containing butylated hydroxyl toluene (BHT; 20 μL) at a final concentration of 5 mM. Each 200 μL of sample was mixed with 400 μL of 10% trichloroacetic acid (TCA) and centrifuged at 12000×g for 5 minutes at 4° C. Then 300 μL of samples or standards at required concentration were added into respective screw capped vials and incubated at 90° C. for 1 hour. Finally, 200 μL of standards/samples each were added to a black clear bottom plate and fluorescence was measured at Ex/Em: 530/550 nm under bottom-read mode in SpectramaxM2e spectrophotometer. The results of the MDA inhibition studies are summarized in Table 5 and 6.

MDA inhibition (%) was calculated using the following formula:

$$\% \text{ MDA Inhibition} = \frac{MDA \text{ concentration in Induction} - MDA \text{ concentration in Samples}}{MDA \text{ concentration in Induction}} \times 100$$

TABLE 4

| Composition # | dose (μg/ml) | LN17121 μg/mL | LN17121 % GSH | LN17129 μg/mL | LN17129 % GSH | Ratio | % Reduced Glutathione Additive (Calculated) | % Reduced Glutathione Observed |
|---|---|---|---|---|---|---|---|---|
| Composition-15 | 10 | 3.33 LN17121 | 5.18 | 6.66 LN17128 | 28.49 | 1:2 | 33.67 | 52.79 |
| Composition-18 | 10 | 5 LN17132 | 7.78 | 5 LN17127 | 33.73 | 1:1 | 41.51 | 52.06 |
| Composition-26 | 1.11 | 0.55 LN17132 | 9.18 | 0.55 LN17128 | 6.20 | 1:1 | 15.38 | 48.1 |
| Composition-27 | 1.11 | 0.55 LN17124 | 9.18 | 0.55 LN17128 | 5.72 | 1:1 | 14.9 | 26.97 |
| Composition-31 | 1.11 | 0.55 LN17125 | 14.21 | 0.55 LN17129 | 16.94 | 1:1 | 31.15 | 39.25 |
| Composition-32 | 10 | 5 LN17126 | 23.16 | 5 LN17129 | 19.18 | 1:1 | 42.34 | 48.76 |
| Composition-33 | 1.11 | 0.55 | 8.90 | 0.55 | 20.86 | 1:1 | 29.76 | 58.2 |

TABLE 5

| Composition # | LN17133 | | LN17129 | | Ratio | % Inhibition of MDA | |
|---|---|---|---|---|---|---|---|
| | µg/mL | % inhibition | µg/mL | % inhibition | | Additive (Calculated) | Observed at 1.11 µg/ml |
| LN16049F4 | 0.84 | 26.81 | 0.27 | 29.41 | 3:1 | 56.22 | 95.42 |
| LN16049F3 | 0.74 | 23.62 | 0.37 | 40.30 | 2:1 | 63.92 | 89.77 |
| LN16049F2 | 0.555 | 17.71 | 0.555 | 60.46 | 1:1 | 78.17 | 97.19 |
| LN16049F1 | 0.37 | 11.81 | 0.74 | 70.61 | 1:2 | 82.42 | 94.67 |

TABLE 6

| Composition # | dose (µg/ml) | LN17121 | | LN17129 | | Ratio | % inhibition of MDA | |
|---|---|---|---|---|---|---|---|---|
| | | µg/mL | % inhibition | µg/mL | % inhibition | | Additive (Calculated) | Observed |
| Composition-17 | 3.33 | 2.22 | 00 | 1.11 | 1.46 | 2:1 | 1.46 | 40.6 |
| | | LN17123 | | LN17129 | | | | |
| Composition-22 | 1.11 | 0.37 | 4.46 | 0.74 | 25.6 | 1:2 | 30.06 | 85.1 |
| Composition-23 | 1.11 | 0.55 | 6.63 | 0.55 | 19.02 | 1:1 | 25.65 | 32 |
| Composition-24 | 1.11 | 0.74 | 8.93 | 0.37 | 12.8 | 2:1 | 21.73 | 50.9 |
| | | LN17123 | | LN17128 | | | | |
| Composition-25 | 3.33 | 1.66 | 16.74 | 1.66 | 28.11 | 1:1 | 44.85 | 76.9 |
| | | LN17132 | | LN17127 | | | | |
| Composition-26 | 10 | 5 | 00 | 5 | 23.55 | 1:1 | 23.55 | 63.6 |
| | | LN17125 | | LN17129 | | | | |
| Composition-32 | 3.33 | 1.66 | 0.64 | 1.66 | 22.88 | 1:1 | 23.52 | 42.4 |

Example 8

The Synergistic In Vivo Efficacy of LN16013F2 in Lowering the Elevated Serum Levels of AST and ALT in $CCl_4$ Induced Hepatic Damage in Rat Models:

Male Sprague Dawley rats of 8 toll week age were procured and 36 healthy rats were randomized in to 6 groups (G-1 to G-6). The groups are as follows G-1 Naïve control, G-2 Disease Control, G-3 LN17131 (200 mpk), G-4 LN16013F2 (200 mpk), G-5 LN17129 (200 mpk) and G-6 Sylimarin (200 mpk).

Induction:

All the animals except those in vehicle control (G1) group were administered with $CCl_4$ in olive oil (1:1 v/v, 0.5 mL/kg bd wt) on days 12, 18 and 25 using disposable syringe through intraperitoneal route. The G1 group animals received only the vehicle (0.5 mL/kg olive oil) by IP route on the same days (day 12, 18 and 25). All the rats had free access to food and drinking water during the study.

Treatment: Animals were given respective designated treatments daily by oral route from day 5 to 25. The test substances LN17131, LN16013F2 and LN17129 were each suspended in 0.5% sodium CMC solution and administered to animals of groups G3, G4 and G5 respectively at a dose of 200 mg/kg.

Blood Collection and Analysis of AST and ALT Levels:

The animals were fasted overnight (approximately 16-18 hours) prior to blood collection. Water was provided ad libitum during fasting period. Blood samples were collected on day 26 from retro-orbital plexus under mild isoflurane anesthesia with the help of a fine capillary tube. The serum samples were separated by centrifuging the blood samples at 7000 rpm for 10 minutes at 4±2° C. AST and ALT levels (U/L) were tested using clinical chemistry analyser, make ILAB, model ARIES, Italy.

Results:

Statistically significant increase in ALT and AST levels (471.67±131.4; 830±117.8) was observed in $CCl_4$ treated disease control group (G2) when compared to vehicle control (G1) group (85.83±2.01; 238.33±14.64). However, significant reduction in AST and ALT levels were observed in G3, G4 and G5 groups treated respectively with LN17131, LN16013F2 and LN17129 when compared to disease control group (G2). The data is summarized below in Table 7.

TABLE 7

| Treatment | Group | Day 26 | |
|---|---|---|---|
| | | ALT | AST |
| Vehicle control p.o | G1 | 85.83 ± 2.01 | 238.33 ± 14.64 |
| Disease control | G2 | 471.67 ± 131.4 | 830 ± 117.8 |
| LN17131 200 mpk (p.o) | G3 | 255.83 ± 41.12 | 548.33 ± 128.6 |
| LN16013F2 200 mpk (p.o) | G4 | 129.17 ± 20.18 | 334.17 ± 57.34 |
| LN17129 200 mpk (p.o) | G5 | 275 ± 133.9 | 390.83 ± 40.77 |
| Silymarin 200 mpk (p.o) | G6 | 395 ± 148.6 | 570.83 ± 135.02 |

Example 9

Evaluation of hepatoprotective activity of LN16025F1, LN16013F2 and LN16049F1 on Acetaminophen induced hepatotoxicity in Sprague Dawley rats: A group of 53 Sprague Dawley rats were examined for health, 48 were selected for the experiment and randomly assigned to 6 groups, G1, G2, G3, G4, G5 and G6 based on the body weight. Hepatic injury/toxicity was induced in all the animals except those of vehicle control (G1) group by administering Acetaminophen in PBS (900 mg/kg b. wt.) from $8^{th}$ to $14^{th}$ day using disposable syringe through intraperitoneal route, 1 hour after the reference or test item administration. The administered dose volume was 5 mL/kg body weight. Animals in vehicle control (G1) group received intraperitoneal injection of PBS on the same day of Acetaminophen injection also 1 hour after vehicle administration. Rats had free access to food and drinking water during the study. The vehicle control (G1) and disease control (G2) animals received 0.5% CMC-Na once daily orally for 14 days. The animals in G3, G4, G5 and G6 groups received orally 200 mpk of LN16025F1, LN16013F2, LN16049F1 or silymarin respectively once daily for 14 days. The dose volume administered was 10 mL/kg body weight.

The animals were fasted overnight prior to collecting 1.5 ml of blood samples from all the animals on days 9, 12 and day 15 and serum samples were separated by centrifuging the blood samples at 7000 rpm for 10 minutes at 4±2° C. The serum samples were analyzed for aspartate transaminase (AST) alanine transaminase (ALT) and total bilirubin (TB), with conventional kit methods using an ILab Aries, an automatic biochemistry analyzer (Milano, Italy).

ALT and AST are the important hepatic metabolic enzymes. These enzymes will be released from liver into serum, when liver is damaged. Thus, the activities of these enzymes in serum can reflect the degree of liver injury. The experiments showed that acetaminophen markedly increased serum ALT and AST levels in disease control (G2) group as compared with the vehicle control group (G1). However, supplementation of LN16025F1, LN16013F2, LN16049F1 and silymarin to the animals of treatment groups G3, G4, G5 and G6 respectively significantly reduced ALT and AST on days 12 and/or 15. These compositions also significantly reduced the serum bilirubin levels on days 12 and 15. The results obtained day 15 are summarized in table 8 and FIG. 1.

Marked degree of centrilobular vacuolation/degeneration of hepatocytes (Score: 3.50) and minimal to marked degree of pericapsular fibrous connective tissue proliferation mixed with adipocytes (Score: 1.67) were evident in livers of Acetaminophen intoxicated rats in disease control group (G2) indicating induction of hepatotoxicity or hepatic damage. Microscopic examination of livers from G3, G4, G5 and G6 group animals, treated with LN16025F1, LN16013F2, LN16049F1 and Silymarin respectively along with Acetaminophen did not reveal any vacuolation/degeneration of hepatocytes (Score: 0) indicating potential ameliorative effects of these test items against Acetaminophen induced hepatic damage in rats. Only, very minimal degree of pericapsular fibrous connective tissue proliferation/adipocytes (Score: 0.50, 0.33, 0.17 and 0.17) was observed in livers of G3, G4 and G6 group animals. Such lesions were not observed in liver of G5 group animals indicating superior efficacy of LN16049F1.

TABLE 8

| Group | ALT (U/L) Day 15 | AST (U/L) Day 15 | TB (mg/dL) Day 15 |
|---|---|---|---|
| G1-Vehicle control p.o | 61.83 ± 3.28 | 170.50 ± 2.23 | 0.09 ± 0.01 |
| G2-Disease control | 148.17 ± 24.24### | 272.17 ± 37.84### | 0.15 ± 0.02 |
| G3-LN16025F1 200 mg/kg (p.o) | 66.83 ± 2.36*** | 213.00 ± 7.46 | 0.11 ± 0.01 |
| G4-LN16013F2 200 mg/kg (p.o) | 67.00 ± 2.65*** | 209.17 ± 13.37 | 0.11 ± 0.01 |
| G5-LN16049F1 200 mg/kg (p.o) | 71.50 ± 2.91*** | 184.83 ± 6.46** | 0.11 ± 0.01 |
| G6-Silymarin 200 mpk (p.o) | 63.17 ± 3.61*** | 204.33 ± 10.75 | 0.11 ± 0.01 |

Example 10

Evaluation of Hepatopancreatic Protective Activity of Composition-34 on Shrimps.

This experiment was conducted in two ponds at same location and conditions having similar dimensions 2 acres each (8093.71 m2). Water from creek was treated by chlorination and healthy post larva 15 was used for stocking with a density of 50/m2. The salinity varied from 5-8 ppt with a temperature range of 28° C. to 35° C. The shrimps were fed with artificial feed as per the requirement. All water quality parameters were measured from time to time. Composition-34 was used daily in the last feed from DOC-15 till harvest along with feed pellets. 2-5 grams Composition-34 was mixed with a binder and coated feed pellets uniformly. The coated pellets were shade dried for 30 minutes before use.

Result: After stocking survival rates of 81% and 83% were observed for control and test ponds. The ponds were harvested on 120 and 115 days of culture (DOC) with a harvest size of 20 and 22.5 grams in the respective control and test ponds. The final Feed Conversion Ratio (FCR) and Average Daily Growth (ADG) were (1.4 & 1.3) and (0.17 & 0.2) respectively for control and test ponds. These and other test parameters are summarized below in table-9 and FIG. 2.

TABLE 9

| Pond | Control pond | Test pond |
|---|---|---|
| Area acres | 2 | 2 |
| Initia stocking (Shrimp) | 400000 | 400000 |
| Density (numbers/m2) | 01-07-2016 | 01-07-2016 |
| Stocking date | 28 Oct. 2016 | 29 Oct. 2016 |
| Culture period (Days) | 120 | 115 |
| Count (numbers/Kg) | 8.33 | 8.70 |
| Harvest size (g) | 20 | 22.5 |
| Harvest number | 325000 | 333333.33 |
| Survival percentage | 81.25% | 83.33% |
| FCR (Feed conversion ratio | 1.4 | 1.3 |
| ADG (Avg daily growth) | 0.167 | 0.196 |

Example 11

Shrimp Field Experiment:

This experiment was conducted in two ponds at same location and conditions having similar dimensions 2 acres each (8093.71 $m^2$). Water from creek was treated by chlorination and healthy *Litopenaeus vannamei* shrimp post larva 15 was used for stocking with a density of 50/$m^2$.

The shrimps were fed with standard feed as per the requirement. All water quality parameters were measured from time to time. Composition-34™ was mixed with feed pellet using a suitable binder. Test Pond and control pond were inoculated with (*Vibrio* Spp) *Vibrio parahaemolyticus* on day 40. In test pond shrimps were fed with Composition-34 as mentioned above. No disease was observed in Test pond 5-7 days after treatment with medicament. Disease aggravated in the control pond 5 days after inoculation. Histopathological examination showed significant improvement in reduction of inflammation, sloughing and vacuoles as summarized FIG. 3.

Example 12

Fish Field Experiment:

This experiment was conducted in two ponds at same location and conditions having similar dimensions 5 acres each (20234.3 m$^2$). Water from creek was treated by chlorination and healthy *Labeo rohita* fish 6 months old was used for stocking with a density of 3000 per acre.

Fish were fed with standard feed as per the requirement. All water quality parameters were measured from time to time. Composition-34 was mixed with feed pellet using a suitable binder.

Water in both the experimental ponds was found to be polluted with agricultural pesticides, antibiotics and chemicals. Mortality of fish was observed in both the ponds along with damaged hepatopancreas. Fish in the test pond were treated with Composition-34 daily for a period of 7 days and was given along with the feed as mentioned above. No mortality was observed in the test pond post treatment.

Figure 4A:
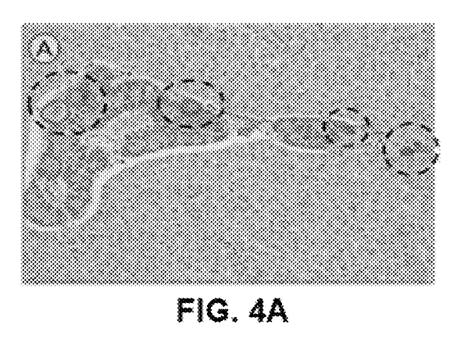
FIG. 4A and FIG. 4B show Liver section of infected Rohu fish with numerous bile pigment deposition (bile stagnation), Moderate degree of inflammation (lymphocyte infiltration) and severe congestion (arrow).
Figure 4B:
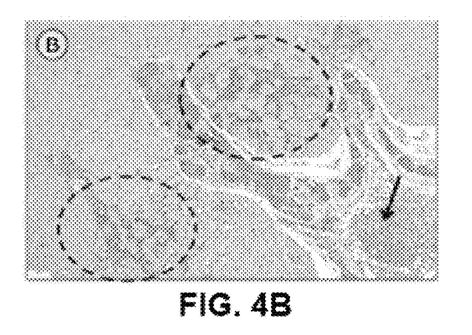
Figure 4C:
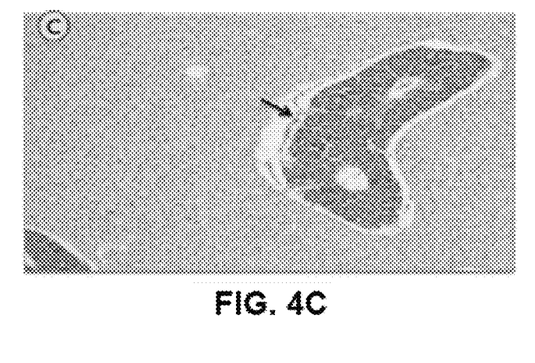
FIG. 4C shows Post treatment with composition 34, the fish liver section shows complete absence of bile pigment granules inside hepatocytes with minimal inflammation (arrow) at the periphery.

Histopathological examination showed significant improvement in reduction of inflammation, accumulated bile pigments, vacuoles and lymphocytes as summarized in FIG. 4.

We claim:

1. An herbal composition for protecting the liver, improving liver health or treating a diseased liver in humans and animals, comprising:
   an effective amount of an extract of *Sphaeranthus indicus*, and
   an effective amount of an extract of *Terminalia chebula*, wherein the extract of *Sphaeranthus indicus* and the extract of *Terminalia chebula* are present in a ratio ranging from 1:3 to 3:1.

2. The herbal composition of claim 1, further comprising:
   at least one biologically active natural ingredient selected from the group consisting of an anti-oxidant, an anti-inflammatory agent, an immunomodulating agent;
   a pharmaceutically acceptable active ingredient;
   a vitamin;
   a mineral;
   a pharmaceutically, nutraceutically, or dietically acceptable excipient, carrier, or diluent; or
   a mixture thereof.

3. The herbal composition of claim 2, wherein the pharmaceutically or dietetically acceptable excipients, carriers and diluents is selected from the group consisting of glucose, fructose, sucrose, maltose, yellow dextrin, white dextrin, aerosil, microcrystalline cellulose, calcium stearate, magnesium stearate, sorbitol, stevioside, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, proteins, calcium salts, pigments, flavors, preservatives, distilled water, saline, aqueous glucose solution, alcohol, propylene glycol and polyethylene glycol, a vegetable oil, an animal oil, white soft paraffin, paraffin, flavorants, colourants, wax, and a mixture thereof.

4. The herbal composition of claim 1, further comprising an agent useful for liver protection, improving liver health and treating liver diseases,
   wherein the agent useful for liver protection, improving liver health and treating liver diseases is selected from the group consisting of extracts of *Aegle marmelos*, *Allium sativum*, *Andrographis paniculata*, *Curcuma longa*, Oscimum *sanctum*, *Phyllanthus amarus*, *Silybum marianum* (milk thistle), *Tephrosia purpurea*, *Tinospora sinensis*, and mixtures thereof.

5. The herbal composition of claim 1, wherein:
   the extract of *Sphaeranthus indicus* is prepared from a *Sphaeranthus indicus* plant part, the *Sphaeranthus indicus* plant part being selected from the group consisting of a fruit, a flower head, a flower, a rind, a seed, leaves, stems, bark, a whole plant, aerial parts of the plant, and mixtures thereof.

6. The herbal composition of claim 1, wherein:
   the extract of *Terminalia chebula* is prepared from a *Terminalia chebula* plant part, the *Terminalia chebula* plant part being selected from the group consisting of a fruit, a flower head, a flower, a rind, a seed, leaves, stems, bark, a whole plant, aerial parts of the plant, and mixtures thereof.

7. The herbal composition of claim 5, wherein the extract of *Sphaeranthus indicus* is prepared by extracting the *Sphaeranthus indicus* plant part with a solvent selected from the group consisting of a C1-C5 alcohols; ketones; chlorinated solvents; water;
   C1-C7 hydrocarbons; esters; and mixtures thereof.

8. The herbal composition of claim 6, wherein the extract of *Terminalia chebula* is prepared by extracting the *Terminalia chebula* plant part with a solvent selected from the group consisting of a C1-C5 alcohols; ketones; chlorinated solvents; water; C1-C7 hydrocarbons; esters; and mixtures thereof.

9. The herbal composition of claim 7, wherein the extract of *Sphaeranthus indicus* is prepared by extracting the *Sphaeranthus indicus* plant part with a solvent selected from the group consisting of ethanol, methanol, n-propanol, isopropyl alcohol, acetone, methyl isobutyl ketone, methylene dichloride, chloroform, water, hexane, ethyl acetate, and mixtures thereof.

10. The herbal composition of claim 8, wherein the extract of *Terminalia chebula* is prepared by extracting the *Terminalia chebula* plant part with a solvent selected from the group consisting of ethanol, methanol, n-propanol, isopropyl alcohol, acetone, methyl isobutyl ketone, methylene dichloride, chloroform, water, hexane, ethyl acetate, and mixtures thereof.

11. A dosage form comprising the herbal composition as claimed in claim 1, wherein the dosage form is selected from the group consisting of a dry powder, a liquid, a beverage, a food product, a dietary supplement, a tablet, a capsule, a soft chewable form, and a gummy candy.

12. The herbal composition as claimed in claim 1, wherein the herbal composition is formulated into:
   a solid food selected from the group consisting of a chocolate bar and a nutritional bar;
   a semisolid food selected from the group consisting of a cream, a jam, and a gel;
   a beverage; or
   a lactic acid bacteria beverage.

13. The herbal composition as claimed in claim 1, wherein the extract of *Sphaeranthus indices* is an organic solvent extract containing:
- from 12 to 30% 7-hydroxyfrullanolide, based on an analysis by HPLC; or
- from 1 to 10% total chlorogenic acids, based on an analysis by HPLC.

14. The herbal composition as claimed in claim 1, wherein the extract of *Terminalia chebula* contains:
- 20% to 80% total polyphenols, based on an analysis by UV spectroscopy; or
- at least one of:
  - 1 to 6% total chebulagic acids;
  - 1-12% total chebulinic acid;
  - 1 to 10% ellagic acid; and
  - 1 to 10% gallic acid,
  - based on an analysis by HPLC.

\* \* \* \* \*